United States Patent [19]

Root-Bernstein

[11] Patent Number: 5,942,491
[45] Date of Patent: *Aug. 24, 1999

[54] METHOD AND COMPOSITIONS FOR TREATING ARTHRITIS

[75] Inventor: Robert S. Root-Bernstein, East Lansing, Mich.

[73] Assignee: Board of Trustees Operating Michigan State University, E. Lansing, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/735,253

[22] Filed: Oct. 22, 1996

[51] Int. Cl.⁶ .......................... A61K 38/04; A61K 38/08; A61K 39/165; A61K 39/145
[52] U.S. Cl. ................. 514/15; 514/12; 514/14; 424/212.1; 424/206.1
[58] Field of Search .................. 514/12, 14, 15; 424/212.1

[56] References Cited

U.S. PATENT DOCUMENTS

| | | | |
|---|---|---|---|
| 5,130,297 | 7/1992 | Sharma et al. | 514/8 |
| 5,194,425 | 3/1993 | Sharma et al. | 514/8 |
| 5,260,422 | 11/1993 | Clark et al. | 530/403 |

FOREIGN PATENT DOCUMENTS

| | | |
|---|---|---|
| WO 92/18150 | 10/1992 | WIPO . |
| 9515384 | 6/1995 | WIPO . |
| WO 95/15384 | 6/1995 | WIPO . |

OTHER PUBLICATIONS

Proost, Paul et al., "Leukocyte Gelatinase B Cleavage Releases Encephalitogens From Human Myelin Basic Protein," *Biochemical and Biophysical Research Communications* 192(3):1175–1181 (1993).
Yamamura et al., *J. of Neuroscience Research* 45(6):706–713 (1996).
Malleson et al., *Arthritis Rheum.* 35(9): Suppl. S137 (1992).
Pelton et al., *Clin. Exp. Immunol.* 62(3):657–661 (1985).
Hogervorst et al., *Infect. Immun.* 59(6):2029–2035 (1991).
Dayhoff, M.O. Atlas of Protein Sequences and Structures, vol. 5, p. 96, Jan. 1972.
Malleson et al. Arthritis Rheum. 35, No. 9, Suppl. S137, Sep. 1992.
Hogervorst et al. Infect Immun. 59(6), 2029–35, Jun. 1991.
Pelton et al. Clin. Exp. Immunol 62 (3) 657–661, Mar. 1985.

*Primary Examiner*—Cecilia J. Tsang
*Assistant Examiner*—Michael Borin
*Attorney, Agent, or Firm*—Lahive & Cockfield LLP

[57] ABSTRACT

The present invention provides a process for the treatment of arthritis including the step of administering to an animal or human patient in need of such treatment a plurality of peptides each of which peptides contains a sequence of amino acid residues that is identical to or homologous to residues 110–121 or 152–161 of myelin basic protein. Novel peptides for use in that process are also provided.

13 Claims, 11 Drawing Sheets

FIG. 1C.  * = Eye Infection

RBARTH8

Saline Controls

MBP

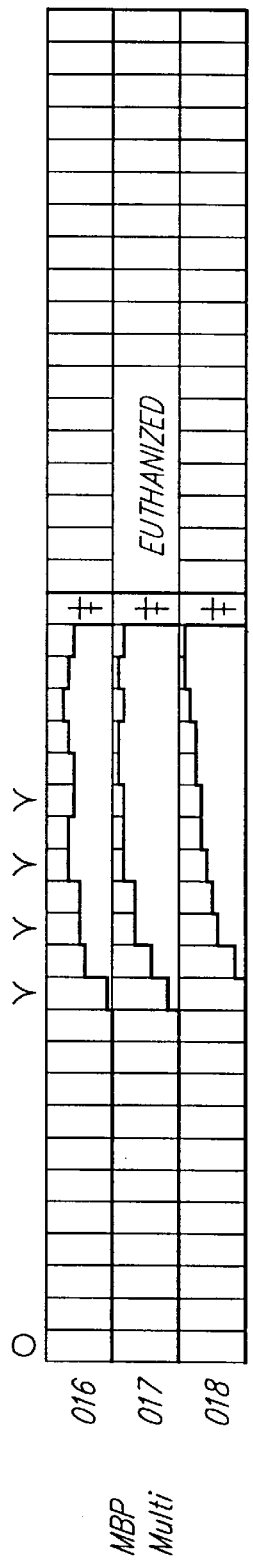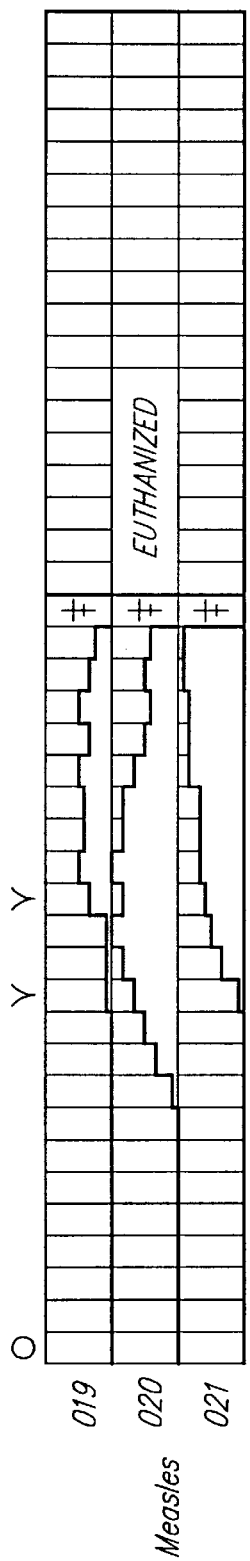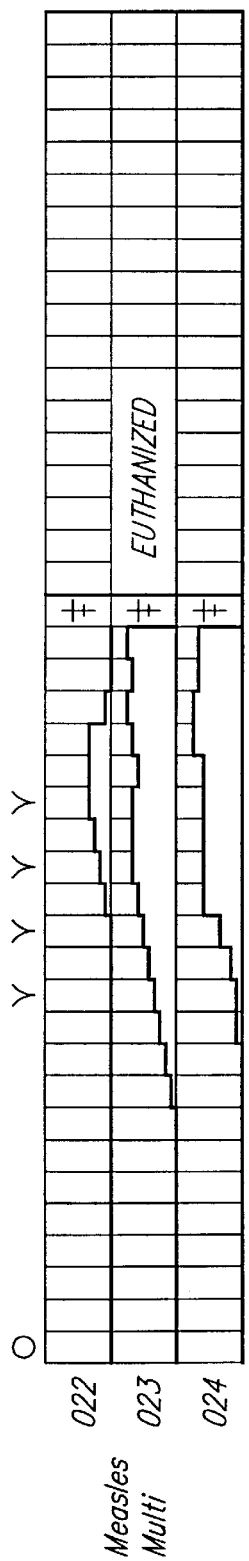

OVAL 1-3

Measles 4-6

Flu 7-9

DPT
10-12

IFA
13-15

RBARTH6
16-18

RBARTH8
19-21 pMBP
22-24

METHOD AND COMPOSITIONS FOR TREATING ARTHRITIS

TECHNICAL FIELD OF THE INVENTION

The field of this invention is the treatment of arthritis. More particularly, the present invention provides a process of treating arthritis using peptides that are identical to or homologous to anti-arthritic portions of myelin basic protein.

BACKGROUND OF THE INVENTION

Arthritis is a very common human bane. Although many animals models of arthritis exist and have been extensively studied, no adequate treatment exists for most forms of arthritis or for related autoimmune diseases with rheumatoid sequelae such as lupus erythematosis. Rheumatoid arthritis presents a particular problem, since it often results in the crippling of affected individuals. While working with one animal model of arthritis (Lewis rats inoculated in the footpad with Mycobacteria, which normally develop adjuvant arthritis), the unexpected observation was made that rats inoculated with a combination of mycobacteria and measles or mycobacteria and measles-mumps-rubella vaccines did not develop arthritis. It was also observed that rats pretreated with porcine myelin basic protein prior to footpad inoculation with mycobacteria were also protected against arthritis. Further experiments showed that the vaccines or MBP were capable of suppressing arthritis once induced.

A literature search has revealed two additional striking observations. First, measles proteins and MBP share extensive regions of homology, suggesting that their common action may share a common mechanism mediated by peptides. This prediction was verified by synthesis of homologous peptides, which also protected and suppressed arthritis. A second observation suggests how important these results may be. Several clinicians have noted that measles infections occasionally mitigate or cure Still's disease, the juvenile form of rheumatoid arthritis. Thus, the treatment regimens described here may represent a significant step towards a treatment or cure for rheumatoid and other forms of arthritis, both in human beings and animals.

BRIEF SUMMARY OF THE INVENTION

The present invention provides a process of treating arthritis in a subject in need of such treatment. The process includes the step of administering to the subject an effective anti-arthritic amount of a plurality of peptides, each of which peptides contains an amino acid residue sequence that is identical to or homologous to a contiguous stretch of at least ten amino acid residues of residues 110–121 or 153–162 of myelin basic protein.

The peptide can be a viral protein such as measles viral protein C, measles viral nucleocapsid protein, influenza viral protein or adenoviral 2.5 protein 21K. Such a viral protein can be contained in an intact virus. In another embodiment, the peptide is myelin basic protein or a fragment thereof.

In another embodiment, the peptide is an isolated and purified synthetic peptide of from 10 to about 50 amino acid residues, preferably containing from 10 to about 40 amino acid residues, more preferably, from 10 to about 30 amino acid residues and, most preferably about 20 amino acid residues.

A preferred peptide for use in a process of the present invention contains the amino acid residue sequence of any of SEQ ID NOs:1–19. Especially preferred peptides have the amino acid residue sequence of any of SEQ ID NOs:1–19.

The present invention further provides an isolated and purified synthetic peptide of from about 15 to about 30 amino acid residues comprising the sequence of any of SEQ ID NOs:14, 15 or 16. A pharmaceutical composition containing an isolated and purified synthetic peptide having the amino acid residue sequence of any of SEQ ID NOs:1–19 is also provided.

BRIEF DESCRIPTION OF THE DRAWINGS

In the drawings that form a portion of the specification.

DETAILED DESCRIPTION OF THE INVENTION

I. The Invention

Figure 1A:
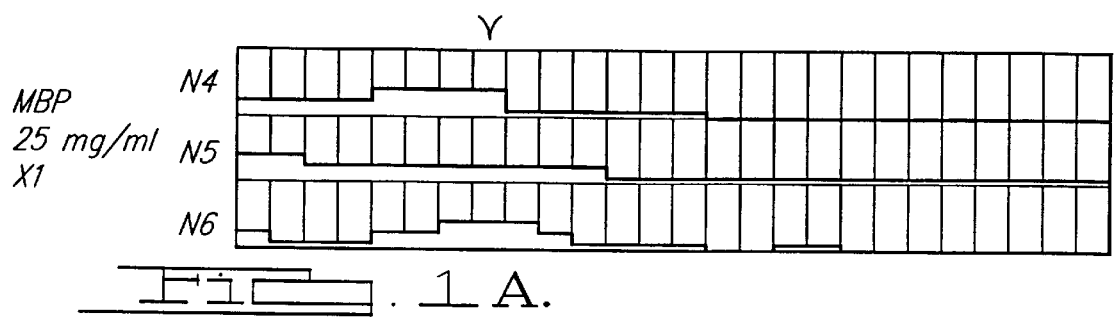
FIG. 1 shows the results of studies involving rats with arthritis for four weeks prior to treatment. Each box represents a single day. The amount of black within a box represents an aggregate arthritic score of two hind legs (FIG. 1) in which the vertical dimension of the box equals eight units (0 to 4+ for each limb); or an aggregate arthritic score of all four limbs (FIGS. 2–6) in which the vertical dimension equals sixteen units (0 to 4+ for each limb). The more black area there is within a box, the more severe the arthritis. The less black area there is within a box, the less severe the arthritis. Circles indicate the day upon which inoculations with CFA were made. Triangles indicate the day upon which inoculations with treatment agents were made. The nature of the treatment is indicated to the left of the data.
Figure 1B:
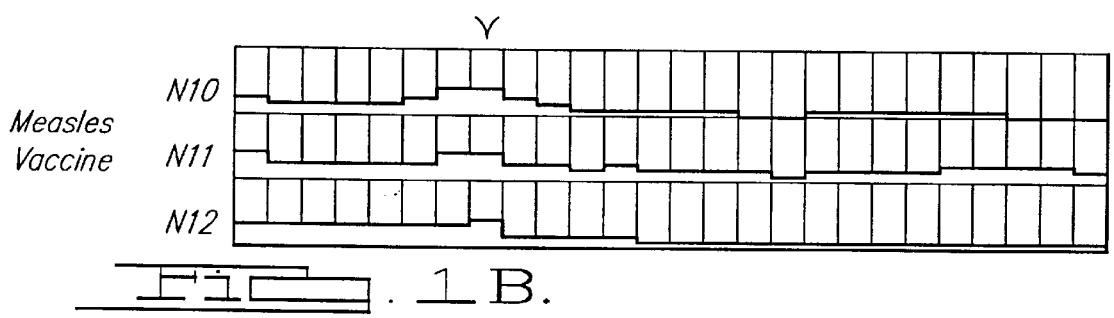
Figure 1D:
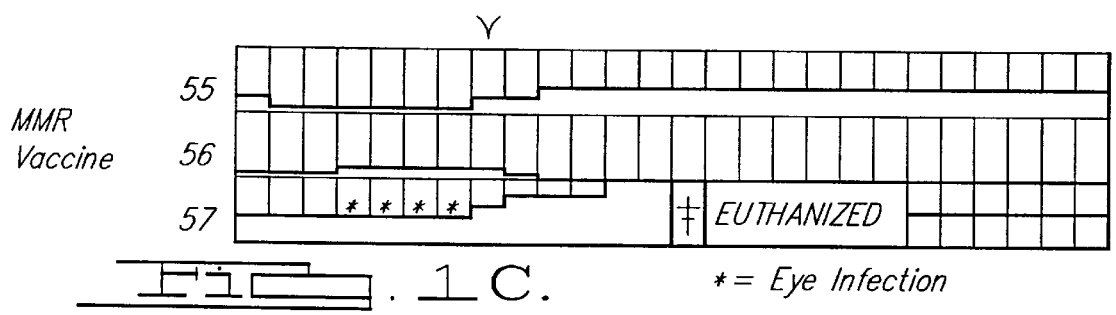
Figure 1D:
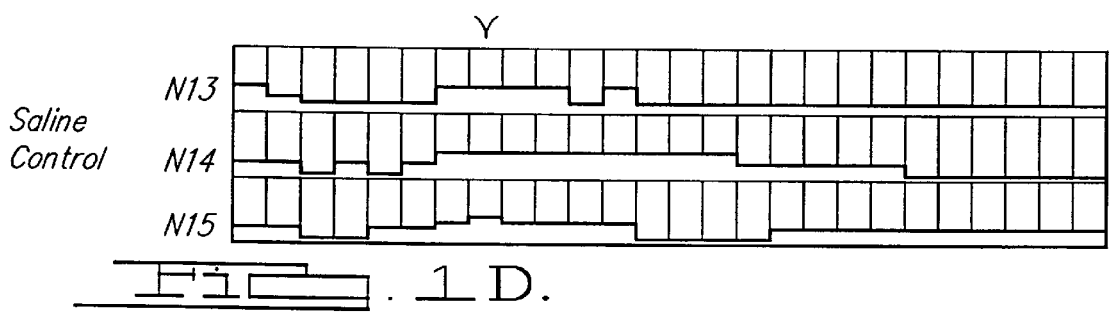
Figure 1E:
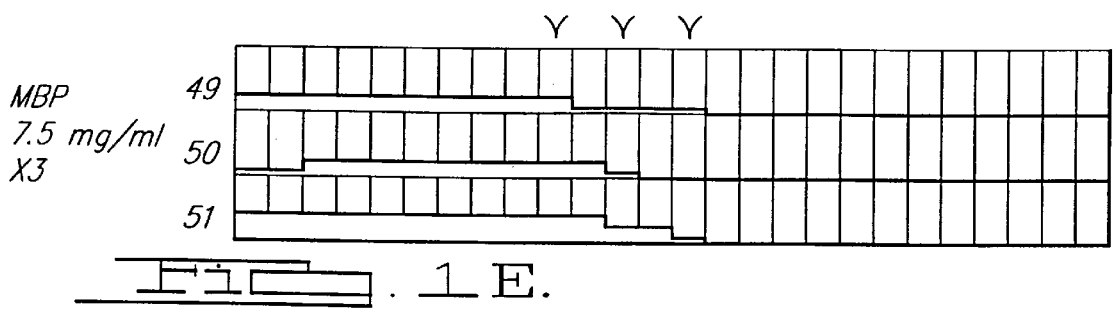
Figure 2A:
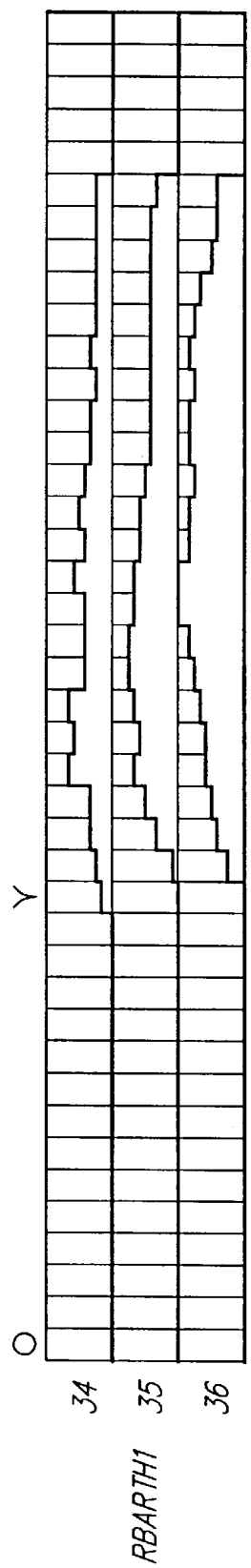
FIG. 2 shows the results of studies using SEQ ID NOs:9–11. Data are expressed as in FIG. 1.
Figure 2B:
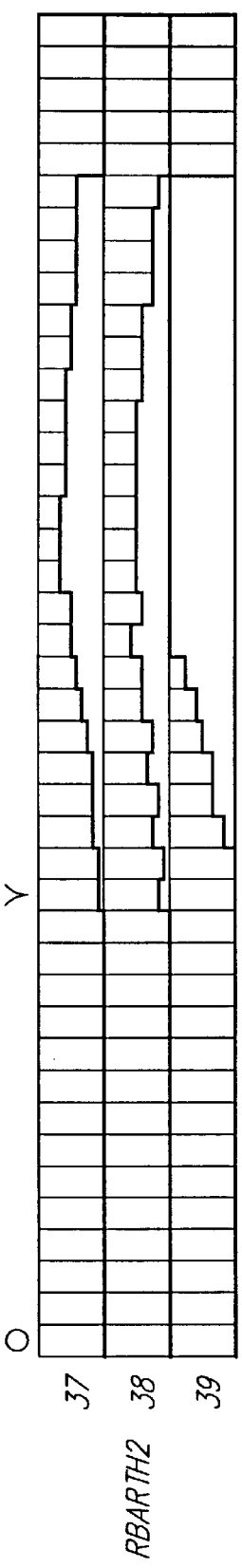
Figure 2C:
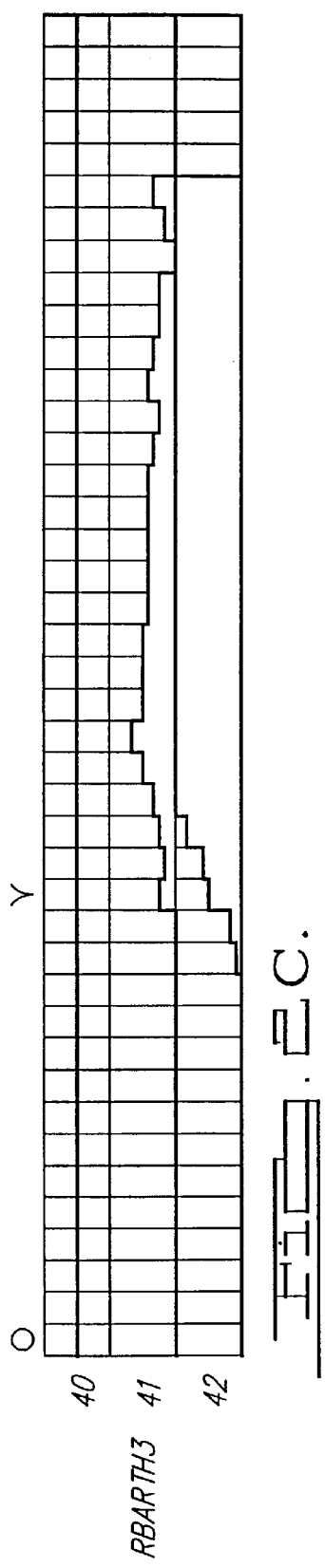
Figure 2D:
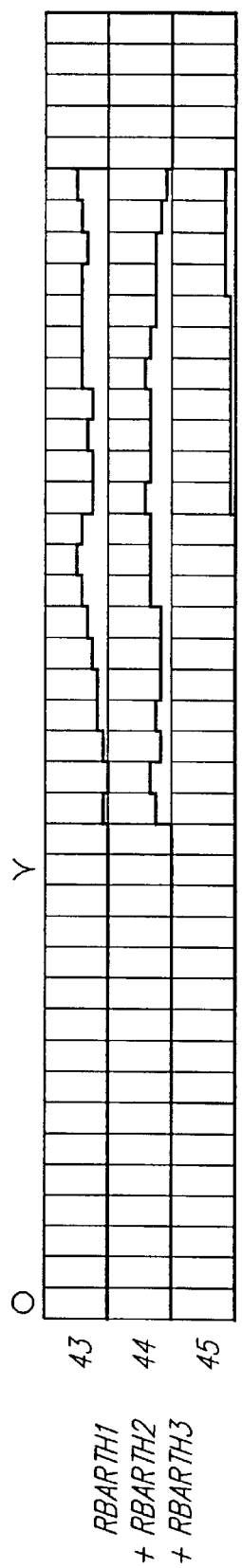
Figure 3A:
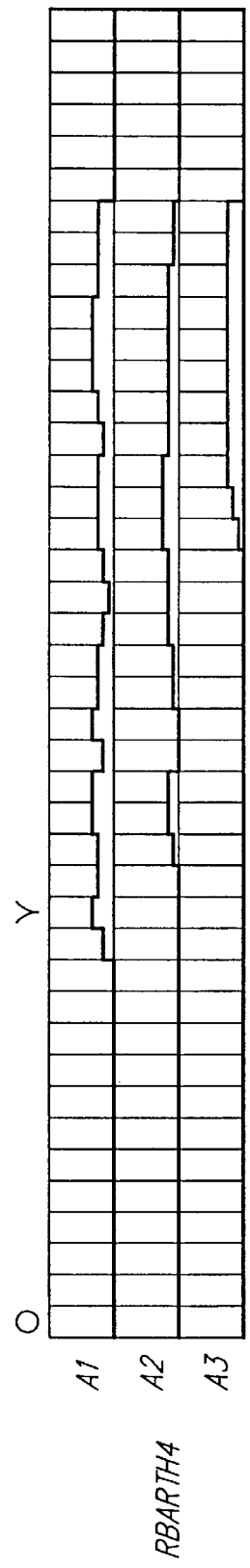
FIG. 3 shows the results of studies using SEQ ID NOS: 12–14. Data are expressed as in FIG. 1.
Figure 3B:
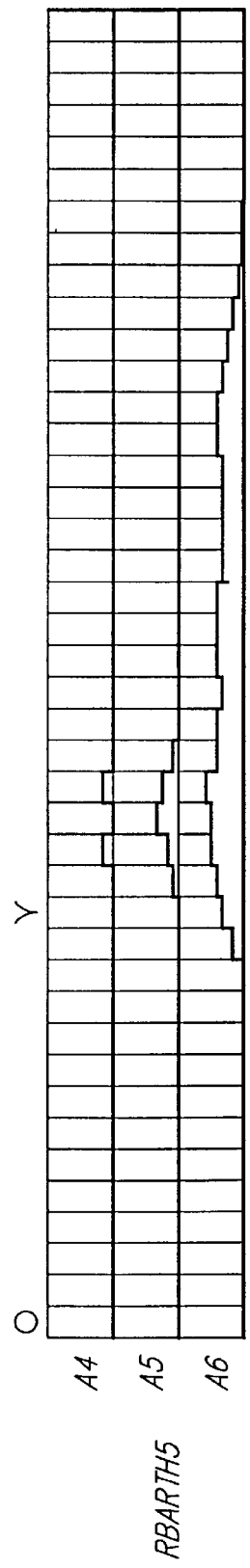
Figure 3C:
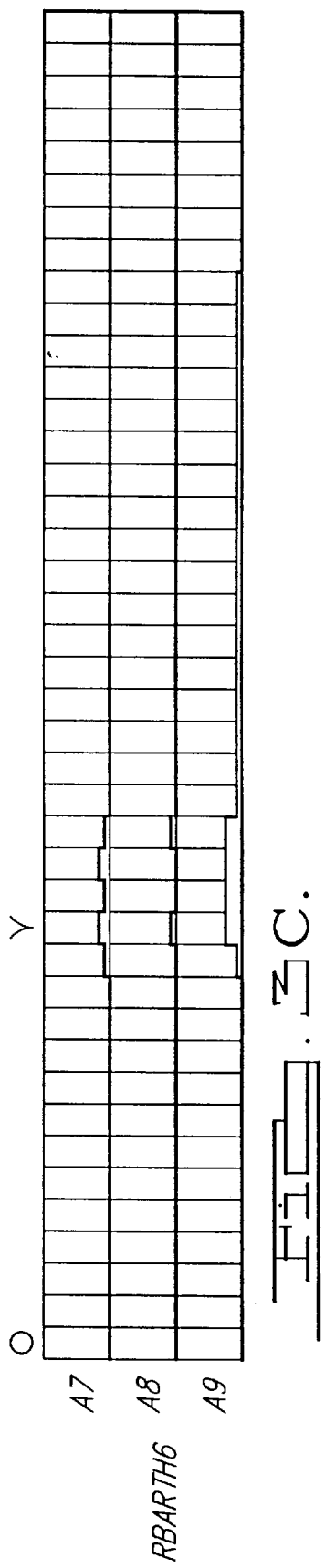
Figure 3D:
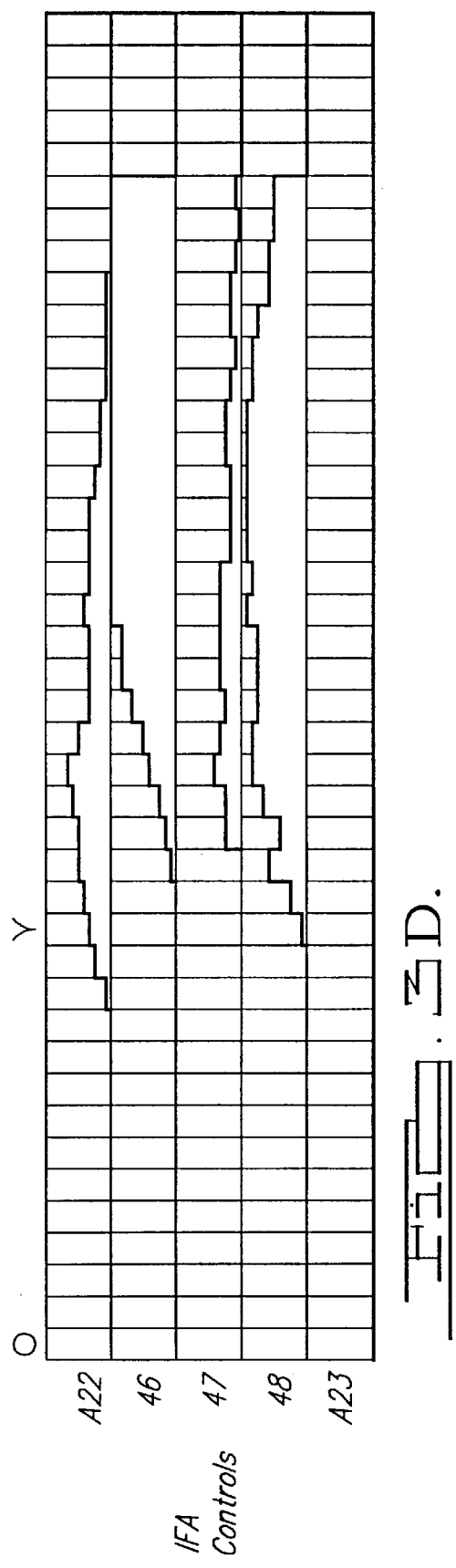
Figure 4A:
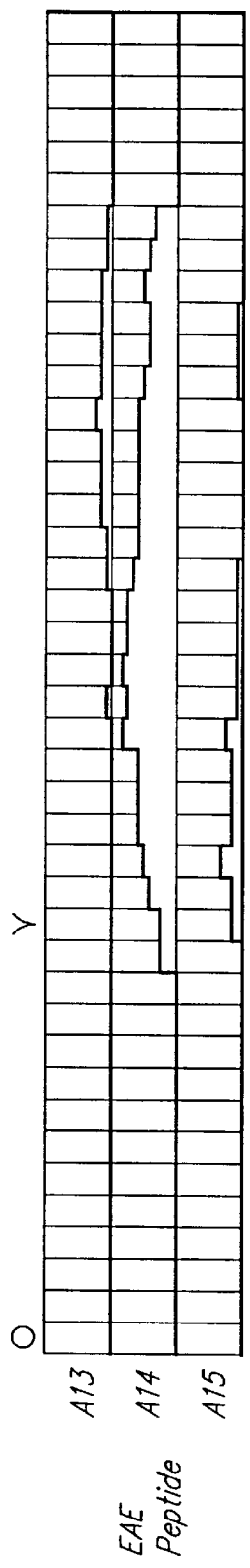
FIG. 4 shows the results of studies using myelin basic protein peptides. Data are expressed as in FIG. 1.
Figure 4B:
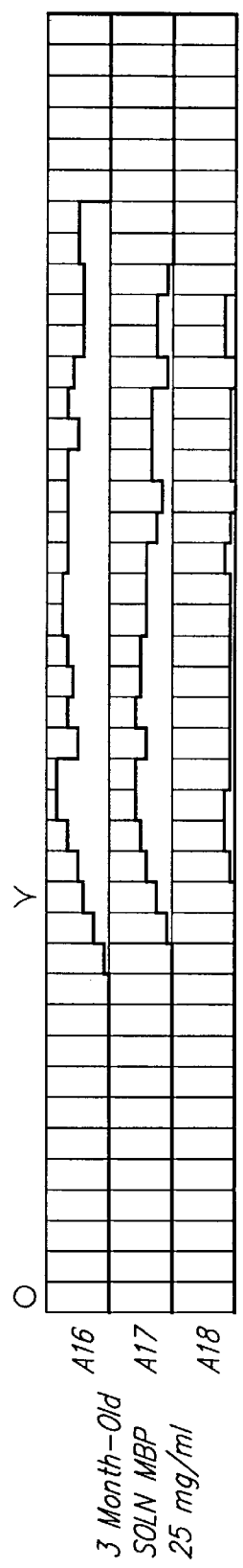
Figure 4C:
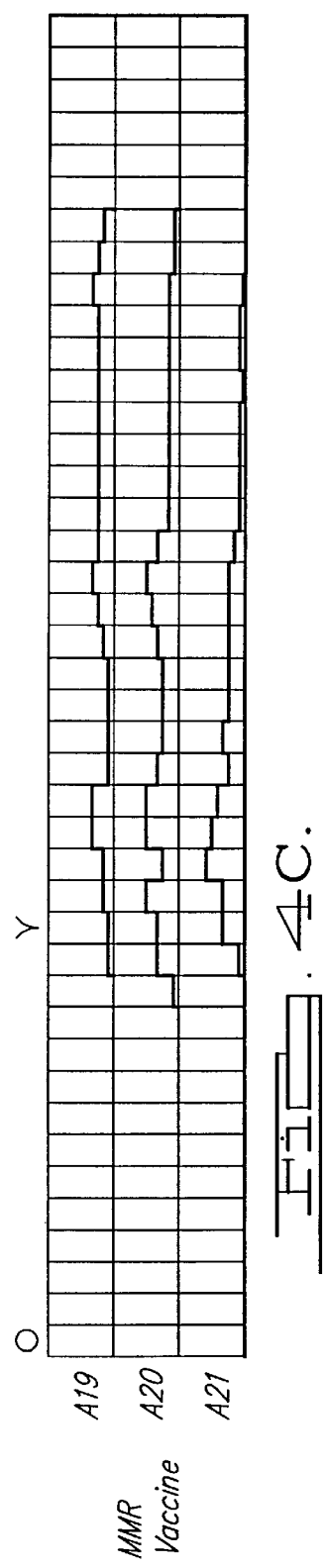
Figure 4D:
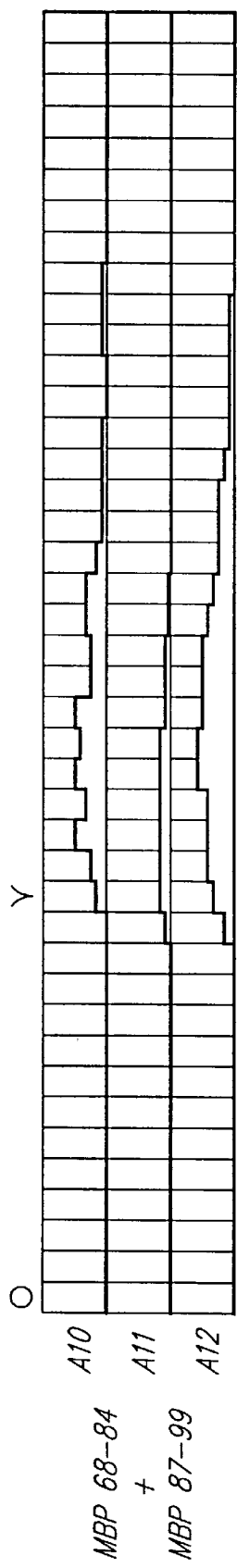
Figure 5A:
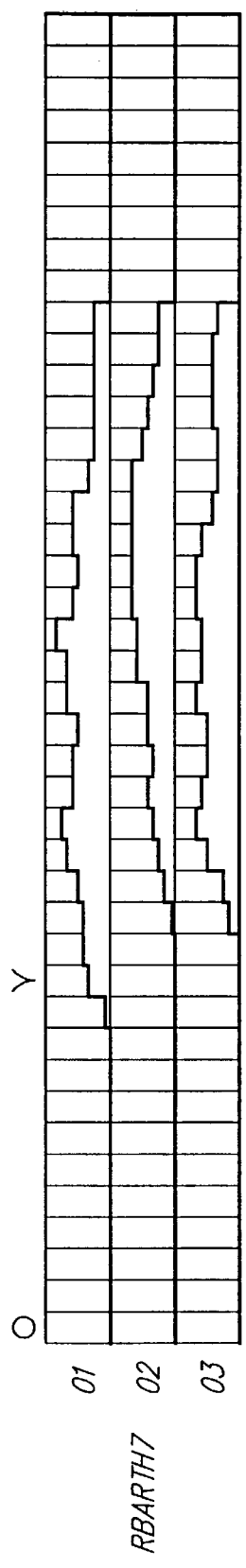
FIG. 5 shows the results of studies using SEQ ID NOs:15–16. Data are expressed as in FIG. 1.
Figure 5B:
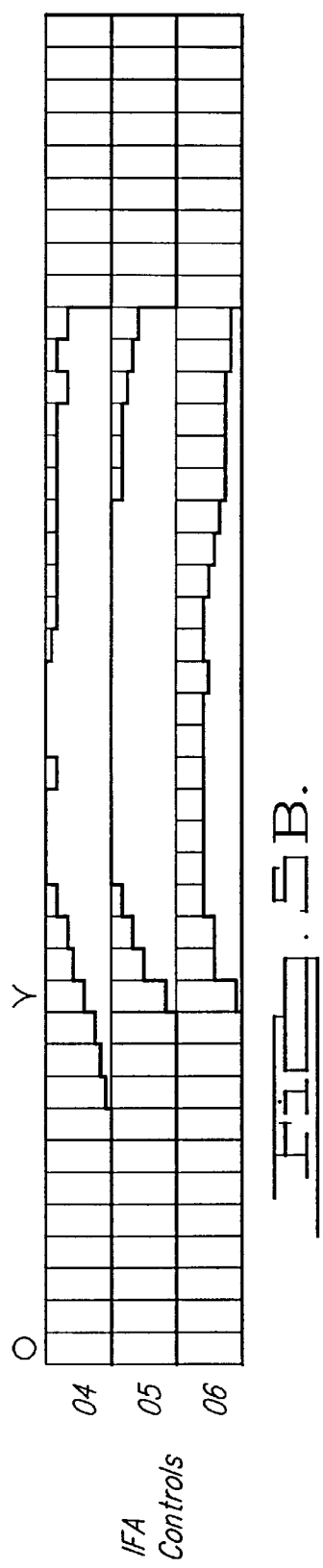
Figure 5C:
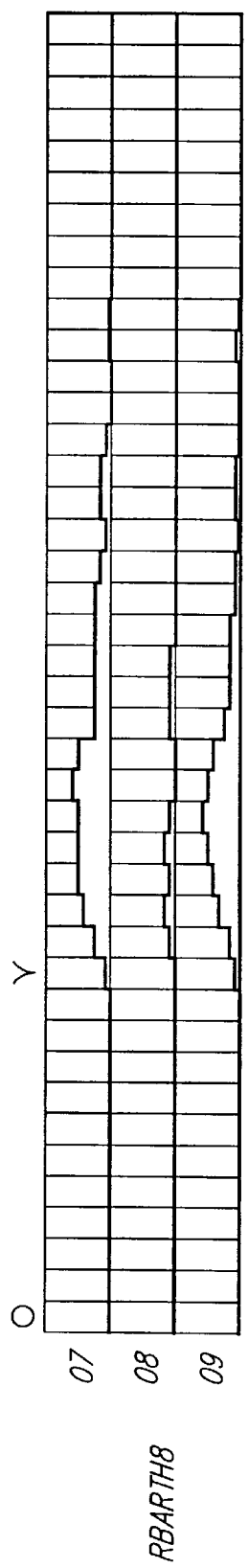
Figure 5D:
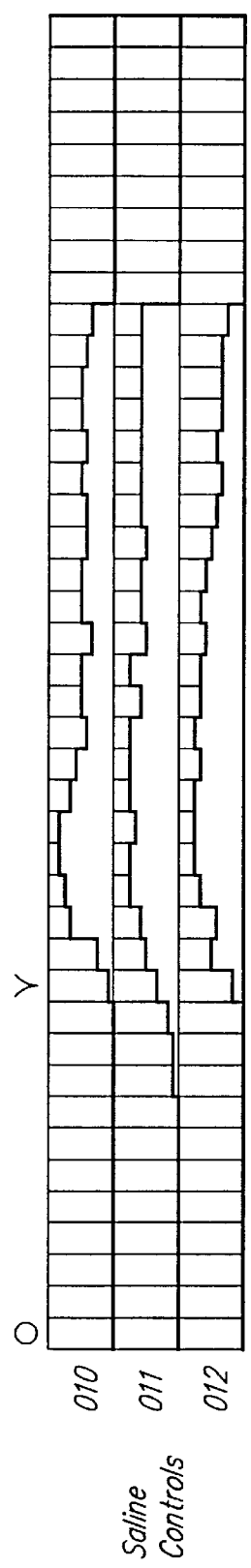

The present invention provides a process for the treatment of arthritis in subjects in need of such treatment and polypeptides, including vaccine proteins, used in such a treatment. The subject can be animal such as a dog or a horse or a human.

II. Anti-Arthritic Peptides, Polypeptides and Proteins

Treatment of a subject with myelin basic protein (MBP) is shown herein to alleviate or prevent the onset of arthritis. The present inventor has discovered that the anti-arthritic activity of MBP is localized to two distinct regions or portions of MBP. Those anti-arthritic portions of MBP are found in MBP between about residue 110 and about 162 of MBP, wherein residue number 1 is the amino-terminal residue. More particularly, the anti-arthritic portions of MBP are found at residues 110–121 and residues 153–162. Residues 110 to 121 of MBP have the sequence Ser-Leu-Ser-Arg-Phe-Ser-Trp-Gly-Ala-Glu-Gly-Gln (SEQ ID NO:1). Residues 153 to 162 of MBP have the sequence Ile-Phe-Lys-Leu-Gly-Gly-Arg-Asp-Ser-Arg (SEQ ID NO:2).

The present inventor has further discovered that polypeptides or proteins comprising a sequence of amino acid residues, which sequence is identical to or homologous to SEQ ID NOs:1 and/or 2 also have anti-arthritic activity.

As used herein, the term "homologous" or its grammatical equivalents means that the homologous region must be a continuous sequence of at least ten amino acids achieving a "similarity score" (SS) of at least fifty percent (preferably higher). The "similarity score" (SS) is determined as follows. The regions to be compared are aligned to achieve a maximum score. The SS score is calculated by awarding each identical pair of amino acids in the aligned regions one point and each conserved pair of amino acids in that region half a point. The total points are added and divided by the total number of amino acid residues compared. By way of example, a 50% SS would equal a total score of 5.0 for a ten amino acid aligned pair of sequences, 6.0 for an eleven amino acid aligned pair of sequences, 10.0 for a twenty amino acid aligned pair of sequences, etc. At most one insertion or one deletion can be made in one of the sequences to maximize alignment scores.

As used in calculating homology, conserved amino acids substitutions are defined in bracketed groups as follows: [Phe, Tyr, Trp]; [Phe, Leu, Ile, Val]; [Arg, Lys, His]; [Glu, Asp, Ser]; [Glu, Gln, Asp, Asn]; [Ser, Thr]; [Thr, Ala]; and [Ala, Gly].

Based on the above definition, a number of amino acid sequences have been identified as being homologous to portions of MBP. By way of example, Jahnke et al. reported that portions of certain viral proteins are homologous to MBP. By way of example, residues 1–10 of measles viral protein C (Met-Ser-Lys-Thr-Glu-Trp-Asn-Ala-Ser-Gln, SEQ ID NO:3) are homologous to residues 111–120 of MBP: residues 142–151 of measle's viral nucleoprotein (Ser-Arg-Phe-Gly-Trp-Phe-Glu-Asn-Lys-Glu, SEQ ID NO:4) are homologous to residues 112–121 of MBP; residues 429–438 of measles viral nucleocapsid protein (Leu-Pro-Arg-Leu-Gly-Gly-Lys-Glu-Asp-Arg, SEQ ID NO:5) are homologous to residues 153–162 of MBP; residues 197–206 of Influenza A/Udorn/72 viral $NS_1$ protein (Thr-Leu-Gln-Arg-Phe-Ala-Trp-Gly-Ser-Ser, SEQ ID NO:6) are homologous to residues 110–119 of MBP; residues 198–207 of Influenza A/Udorn/72 viral $NS_1$ protein (Leu-Gln-Arg-Phe-Ala-Trp-Gly-Ser-Ser-Asn, SEQ ID NO:7) are homologous to residues 111–120 of MBP; and residues 27–38 of Adenoviral 2.5 early 21K protein (Phe-Trp-Arg-Phe-Leu-Trp-Gly-Ser-Ser-Gln, SEQ ID NO:8) are homologous to residues 111–120 of MBP.

The present invention further provides isolated and purified synthetic peptides that contain a sequence of amino acids that is homologous to residues 110–121 and/or residues 153–162 of MBP, which peptides have anti-arthritic activity. Exemplary and preferred such peptides contain the amino acid residue sequences: Met-Ser-Lys-Thr-Glu-Trp-Asn-Ala-Ser-Gln (SEQ ID NO:9); Ser-Arg-Phe-Gly-Trp-Phe-Glu-Asn-Lys-Glu (SEQ ID NO:10); Leu-Pro-Arg-Leu-Gly-Gly-Lys-Glu-Asp-Arg (SEQ ID NO:11); Thr-Leu-Gln-Arg-Phe-Ala-Trp-Gly-Ser-Ser-Asn (SEQ ID NO:12); Phe-Trp-Arg-Phe-Leu-Trp-Gly-Ser-Ser-Gln (SEQ ID NO:13); Met-Ser-Lys-Thr-Glu-Trp-Asn-Ala-Ser-Gln-Ser-Arg-Phe-Gly-Trp-Phe-Glu-Asn-Lys-Glu (SEQ ID NO:14); Leu-Pro-Arg-Leu-Gly-Gly-Lys-Glu-Asp-Arg-Ser-Arg-Phe-Gly-Trp-Phe-Glu-Asn-Lys-Glu (SEQ ID NO:15); and Met-Ser-Lys-Thr-Glu-Trp-Asn-Ala-Ser-Gln-Leu-Pro-Arg-Leu-Gly-Gly-Lys-Glu-Asp-Arg (SEQ ID NO:16).

A peptide of the present invention is at least 10 amino acid residues in length. Preferably, the peptide contains from 10 to about 50 residues, more preferably from 10 to about 40 residues, even more preferably from 10 to about 30 residues and, most preferably from 10 to about 20 residues. A peptide of the present invention can contain more than one sequence of ten amino acid residues that are homologous to MBP. Those sequences can be homologous to the same (e.g., residues 110–121) or different (e.g., residues 110–121 and 153–162) portions of MBP.

The present invention further provides a pharmaceutical composition comprising a peptide of this invention together with a physiologically acceptable diluent. The peptides are formulated into compositions together with one or more non-toxic physiologically tolerable or acceptable diluents, carriers, adjuvants or vehicles that are collectively referred to herein as diluents, for administration to subject. The compositions can be administered to humans and animals either orally, locally (powders, ointments or drops), as a nasal spray or as a suppository.

Suitable pharmaceutical composition may comprise physiologically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

An especially preferred pharmaceutical composition contains peptides dissolved in an aqueous medium or solvent. The aqueous composition can then be admixed under sterile conditions with physiologically acceptable diluents, preservatives, buffers or propellants as may be required to form a spray or inhalant.

Actual dosage levels of peptides in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

III. Process of Treating Arthritis

In another aspect, the present invention provides a process of treating arthritis in a subject in need of such treatment. The process includes the step of administering to the subject an effective anti-arthritic amount of a plurality of peptides each of which contains an amino acid residue sequence that is identical to or homologous to a contiguous stretch of at least ten amino acid residues of residues 110–121 or 153–162 of myelin basic protein.

The polypeptide can be an intact protein, fragments of such proteins having anti-arthritic activity or an isolated and purified peptide as disclosed above. An exemplary intact protein is MBP. In another embodiment, the intact protein is a viral protein such as a measles, influenza or adenoviral protein. Exemplary and preferred such proteins are measles viral protein C, measle's viral nucleocapsid protein, Influenza A/Udorn/72 viral $NS_1$ protein, and Adenoviral 2.5 early 21K protein.

Measles vaccines (e.g., Merck) have previously been approved for prevention of measles infections, but have not been used previously as a treatment for arthritis. Measles vaccine and MMR vaccine are shown herein to prevent and to suppress adjuvant arthritis in Lewis rats, an art accepted standard pharmaceutical model for screening anti-arthritic drugs. Although there are a few anecdotal reports of wild-type measles infections occasionally resulting in remissions and even cures of Still's disease, the juvenile form of rheumatoid arthritis, there is no report of the use of measles viral proteins for a similar purpose.

Influenza vaccine (e.g., Parke-Davis's Fluogen) has previously been approved for prevention of influenza infections. Influenza vaccine is shown herein to prevent and to suppress adjuvant arthritis in Lewis rats.

Porcine myelin basic protein (Lilly) has previously been approved for use as an experimental drug for the treatment of multiple sclerosis, but has not been used previously as a treatment for arthritis. MBP is shown herein to prevent and suppress arthritis.

Viral proteins can be administered as isolated proteins or as part of intact viruses. By way of example, administration of measles viral proteins can be in the form of vaccines [e.g., Measles Virus Vaccine (M), Live MSD Atenuvax and Measles, Mumps, Rubella Virus Vaccine Live, MSD, MMRII (MMR) (Merck, Sharp and Dohme, West Point, Pa.); Influenza Virus Vaccine, Trivalent, Types A and B Fluogen (1987–88) (Parke-Davis, Morris Plains, N.J.)]. A detailed description of the treatment of arthritis using MBP and a variety of vaccines is set forth hereinafter in the Examples.

In an especially preferred embodiment, the polypeptide is an isolated and purified peptide as set forth above. Exemplary and preferred such peptides comprise any of SEQ ID NO:9, 10, 11, 12, 13, 14, 15 or 16. Such a peptide is preferably administered to the subject in a pharmaceutical composition as disclosed above. A detailed description of the anti-arthritic activity of such peptides is set forth hereinafter in the Examples.

A process of the present invention can be used to treat subjects suffering from arthritis or as a prophylactic treatment for preventing the onset of arthritis. Examples 2 and 3, hereinafter, demonstrate both the attenuation of pre-existing arthritis and the prevention of arthritis onset using a process of the present invention.

The Examples that follow illustrate preferred embodiments of the present invention and are not limiting of the specification and claims in any way.

EXAMPLE 1

General Procedures

Studies were performed using the adjuvant-induced model of arthritis in Lewis rats, which model is an accepted model for studying human arthritis.

Figure 6A:
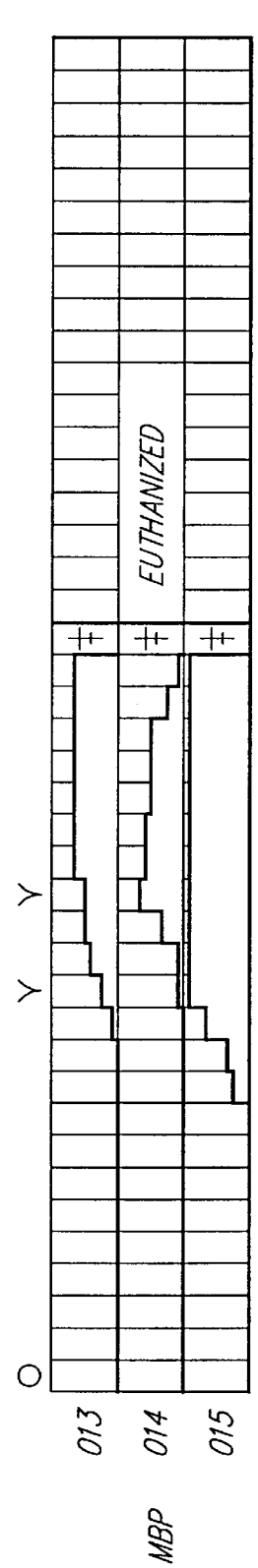
FIG. 6 shows the results of control studies with myelin basic protein and measles vaccine. Data are expressed as in FIG. 1.
Figure 7A:
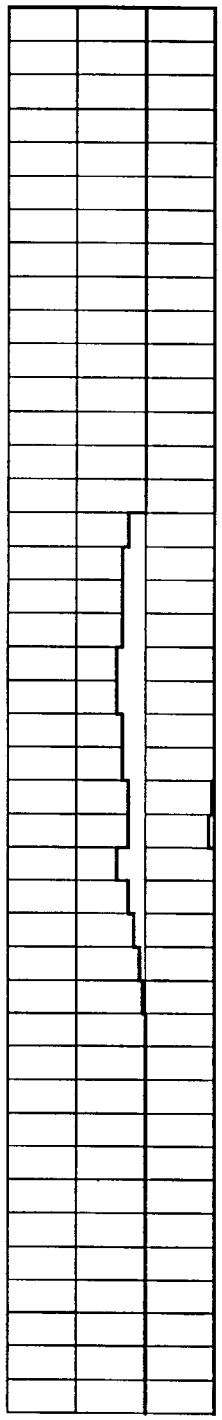
FIG. 7 shows the results of studies using various vaccines. Data are expressed as in FIG. 1.
Figure 7B:
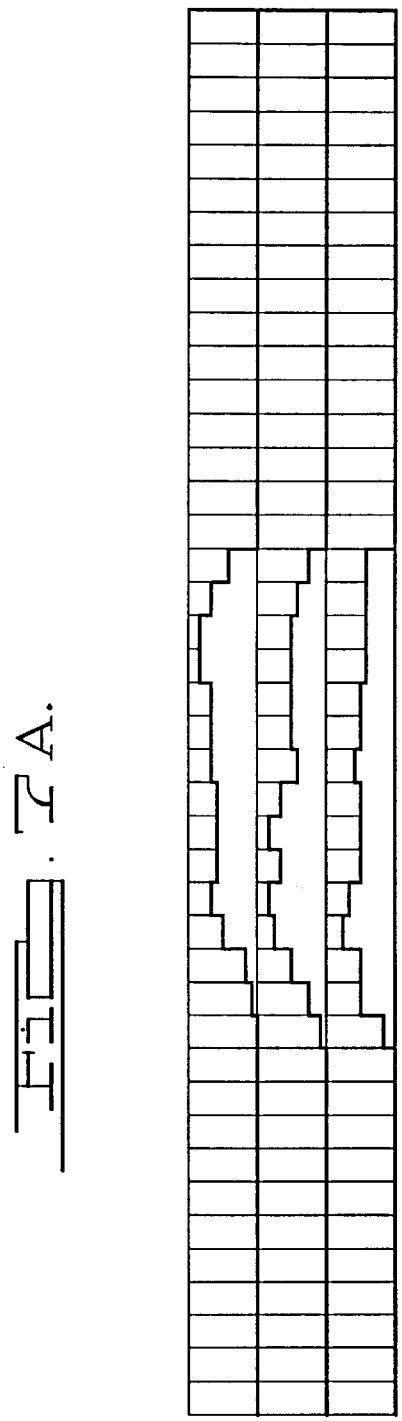
Figure 7C:
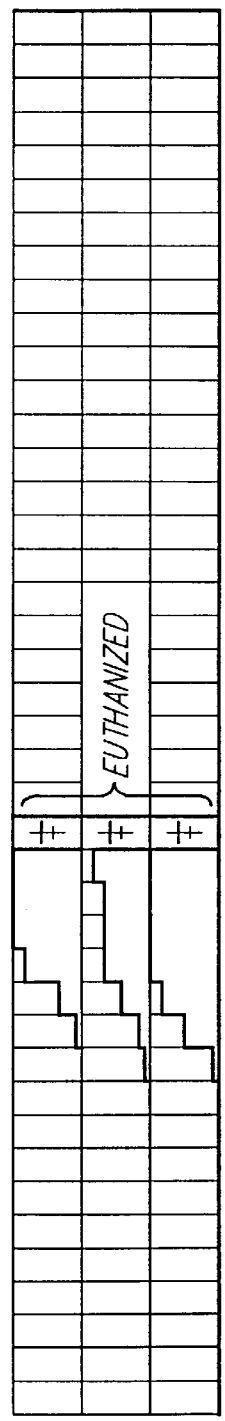
Figure 7D:
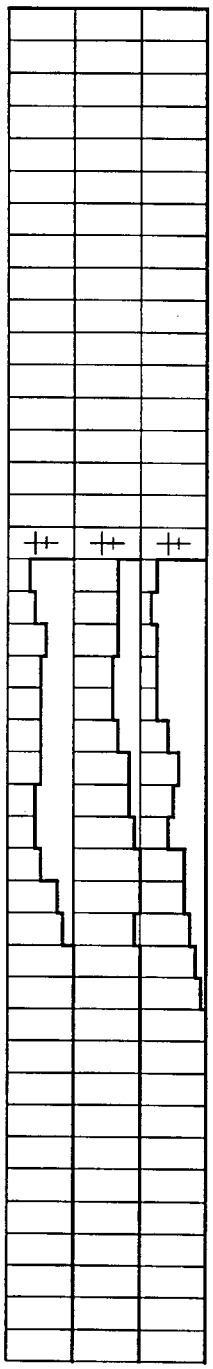
Figure 8A:
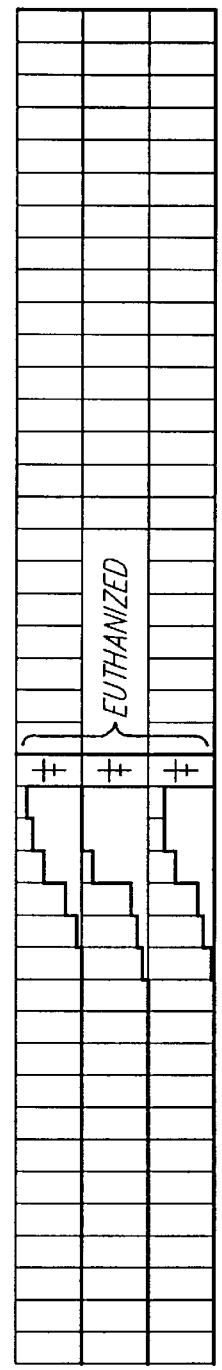
FIG. 8 shows the results of studies using SEQ ID NOs:14 and 16. Data are expressed as in FIG. 1.
Figure 8B:
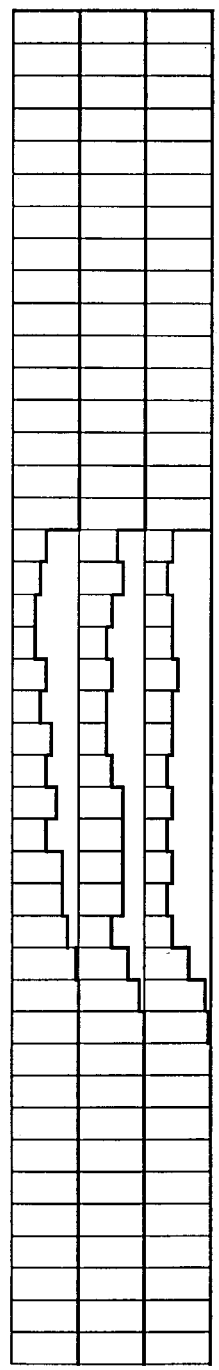
Figure 3C:
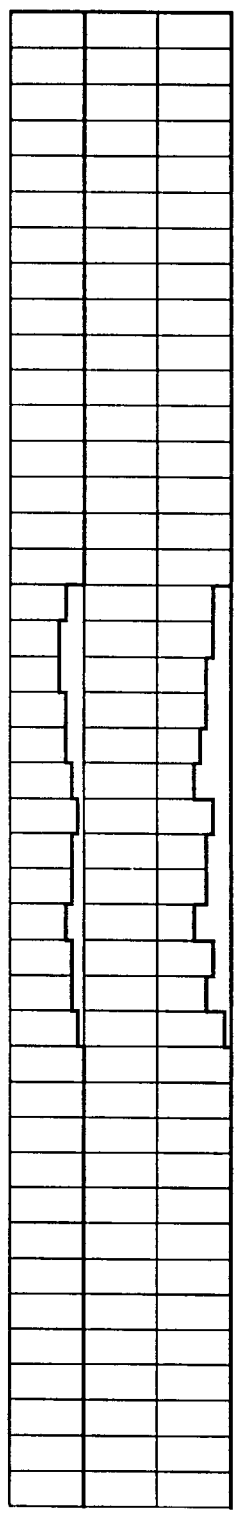
Figure 3D:
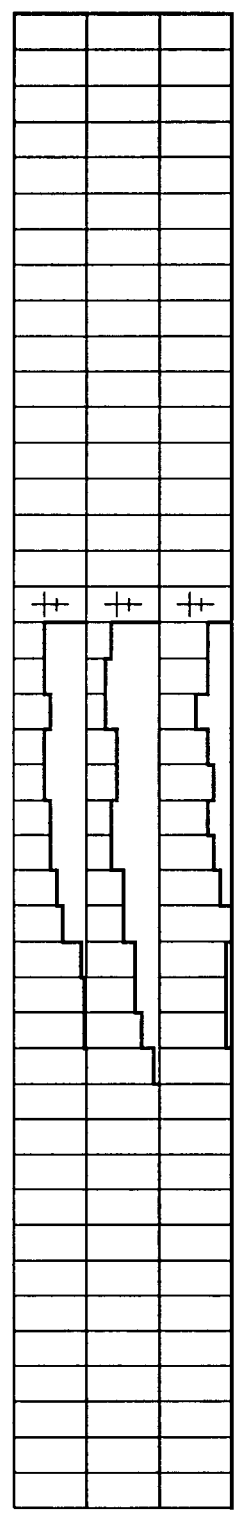

Three types of studies were performed. First, groups of three rats were inoculated subcutaneously in their back between their shoulders with a test peptide or polypeptide (FIGS. 6–8). Six weeks later, these rats were inoculated with an arthritis-inducing adjuvant (FCA) at the base of their tail. The purpose of these experiments was to determine whether pre-inoculation with the vaccines prevented or delayed onset of arthritis.

In the second set of studies (Table 1), each rat was inoculated in the right hind footpad with an emulsion composed of bacterial antigens in complete Freund's adjuvant (FCA) and a test peptide or polypeptide in pyrogen-free physiological saline. The purpose of these experiments was to determine whether vaccines combined with FCA would alter the outcome of the FCA inoculation.

In a third set of studies, arthritis was induced in rats using FCA inoculated at the base of their tail. Between days 12 to 15 (FIGS. 2–5), or at day 28 (FIG. 1), groups of three animals were inoculated subcutaneously between their shoulders with a test peptide or polypeptide. The purpose of these experiments was to determine if it was possible to suppress arthritis once present.

In all studies, rats were weighed and examined every day, note made of any unusual symptoms, and the extent and severity of arthritis noted. Several controls were run for the experiments. In all experiments, some groups of animals were given inoculations with the carrier material used in the experiments, i.e., either IFA or saline solution. The same number of inoculations were given according to the same regimen for the controls as for the treated animals. In some cases, IFA, saline, and non-treated controls were all run simultaneously. No obvious differences were observed.

All rats were treated according to animal use approved protocols. They were weighed and examined every day, note made of any unusual symptoms, and the extent and severity of arthritis (if present) noted. A scale of 1 to 4 (4 being the most severe) was used to evaluate the extent of the arthritis in each limb separately. A total scale of either 8 (hind limbs only) or 16 (all limbs) was used for plotting the results of the experiments. Most experimental protocols were performed on groups of 3 rats although some groups consisted of 5 rats, or were repeated so that 6 total were used. Animals that developed exacerbated symptoms due to treatment were euthanized.

EXAMPLE 2

Studies with Vaccines

Vaccines used in these studies are indicated below together with their commercial source. Mb was obtained as complete Freund's adjuvant from Difco (Detroit, Mich.); the Mt from Difco as a dry powder and mixed with incomplete Freund's adjuvant to create a 5mg/ml complete adjuvant (FCA). The following vaccines were used: Measles Virus Vaccine (M), Live MSD Atenuvax and Measles, Mumps, Rubella Virus Vaccine Live, MSD, MMRII (MMR) (Merck, Sharp and Dohme, West Point, Pa.); Influenza Virus Vaccine, Trivalent, Types A and B Fluogen (1987–88) (Parke-Davis, Morris Plains, N.J.); Diphtheria and Tetanus Toxoids and Pertussis Vaccine Adsorbed (DTP) (Michigan Department of Public Health, Lansing, Mich.); and Bacillus Calmette-Guerin (BCG) Porcine myelin basic protein (pMBP).

In a first study, groups of three rats were inoculated subcutaneously in their back between their shoulders with 0.1 ml FCA, M, MMR, Flu, DTP, BCG, or PMBP. The vaccines were diluted to one fifth of their recommended human strength in pyrogen-free physiological saline. PMBP was used at a strength of 75 mg/ml. Six weeks later, these rats were inoculated with 0.05 ml FCA (Mt) at the base of their tail.

In a second study, each rat was inoculated in the right hind footpad with 0.05 ml of emulsion composed of bacterial antigens in incomplete Freund's adjuvant (IFA) and a viral vaccine or gpMBP in pyrogen-free physiological saline. Inoculations including a mycobacteria contained 100 μg Mb or Mt. The vaccines were prepared by bringing them to standard human strength according to package instructions (if necessary) and then diluting 1:10 in pyrogen-free physiological saline. Each inoculation contained 0.025 ml of this diluted vaccine preparation. Higher concentrations of flu vaccine were prepared by diluting 1:2 in saline (Flu 5) and without dilution (Flu 10). Inoculations incorporating porcine myelin basic protein (BP) contained 25 μg of the protein in pyrogen-free physiological saline.

In a third study, arthritis was induced in rats using 0.05 ml FCA (Mt) inoculated at the base of their tail. At either day 8 or day 15, groups of three animals were inoculated subcutaneously between their shoulders with 0.1 ml M, MMR, or MBP. Vaccines were full human strength. MBP was 75 mg/ml in pyrogen free physiological saline.

Results are summarized in Table 1 and FIGS. 1 through 8.

TABLE 1

INCIDENCE AND SEVERITY OF ADJUVANT ARTHRITIS AS A FUNCTION OF VACCINE-BACTERIUM COMBINATION

|  | M. tuberculosis | | | | M. butyricum | | | | DTP | | | |
| --- | --- | --- | --- | --- | --- | --- | --- | --- | --- | --- | --- | --- |
|  | A | B | C | D | A | B | C | D | A | B | C | D |
| Saline | 10/10 | 6 | 12 | >30 | 7/7 | 6 | 12 | >30 | 0/4 | 0 | N/A | 0 |
| Flu 1 | 2/5 | 2 | 15 | >30 | 5/5 | 4 | 14 | >30 | 0/4 | 0 | N/A | 0 |
| Flu 5 | 4/8 | 2 | 17 | 4 | 2/3 | 2 | 17 | 8 | not done | | | |
| Flu 10 | 2/8 | 2 | 20 | 2 | 1/3 | 2 | 22 | 4 | 0/4 | 0 | N/A | 0 |
| Measles | 0/5 | 0 | N/A | 0 | 0/5 | 0 | N/A | 0 | 0/4 | 0 | N/A | 0 |
| MMR | 0/5 | 0 | N/A | 0 | 0/5 | 0 | N/A | 0 | 0/4 | 0 | N/A | 0 |
| DTP | 6/6 | 6* | 11 | + | 6/6 | 6* | 11 | + | not done | | | |
| BP | not done | | | | 0/6# | 0 | 0 | 0 | not done | | | |

A. Number of animals inoculated/number of animals with arthritis. [#: Developed experimental allergic encephalomyelitis].
B. Severity of symptoms. 6: all four limbs, back and tail; 4: all four limbs; 2: a pair of limbs; 0: no symptoms. [*: extraordinary swelling in all affected joints].
C. Average day of onset of arthritis.
D. Average duration of symptoms (in days). [+: euthanized].

Table 1 shows the results of co-inoculations of FCA with various vaccines. As expected, FCA inoculated by itself induced adjuvant arthritis. No animal co-inoculated with measles vaccine or MMR developed any symptoms of arthritis, however. A small attenuation of symptoms was observed with co-inoculation of influenza vaccine, so higher doses were also explored, and doses ten times that utilized for measles did have a significant protective effect, attenuating the degree of arthritis experienced by the animals and retarding the time of onset. DPT vaccine so dramatically increased the rate of onset and severity of the symptoms that all of the animals so treated had to be euthanized almost immediately.

The observation that some agents could prevent the onset of arthritis immediately brought to mind a similar effect that has been observed, but never explicitly explored, with myelin basic protein (MBP). It is well known that co-administration of MBP with CFA induces experimental allergic encephalomyelitis (EAE), but there are no clinical or pathological signs of arthritis in the affected animals, nor has anyone working with EAE ever reported any. We verified this insight by inoculating six rats with arthritogenic doses of CFA combined with MBP. All six animals developed EAE, but none had any clinical signs or arthritis (Table 1). In light of the protective effect of measles vaccine, the absence of arthritis pathology in EAE becomes very striking, since the doses used for EAE induction are sufficient to induce adjuvant arthritis. Since no arthritis is induced, the MBP must be conferring an anti-arthritic protective effect, even as it creates EAE.

Having observed that measles and influenza vaccines and PMBP protect against arthritis, a second set of experiments were performed in which arthritis was induced, and at the first clinical signs of disease, either measles vaccine, MMR, or pMBP were inoculated sub-cutaneously in saline. Measles and pMBP had a marked effect on the course of the arthritis, reducing the clinical severity of the disease (FIG. 1). Repeated small inoculations of pMBP resulted in complete remission in all three animals tested. Control inoculations using saline solution had no observable effect on disease progression. MMR, however, greatly exacerbated pre-existing arthritis.

EXAMPLE 3

Studies with Peptides

A selection of peptides representing homologies between measles viral protein, an influenza viral protein, an adenoviral protein, and MBP were synthesized by Joseph Leykam and his staff at the Macromolecular Structure and Synthesis Facility of the Biochemistry Department of Michigan State University. Several peptides representing various regions of MBP were also obtained commercially from BAChem Bioscience (King of Prussia, Pa.). Peptides were made up as a 1:1 sterile saline:IFA emulsion (i.e., each animal got ca. 3 mg of peptide) and administered to rats in accordance with the protocols of Example 1. Table 2, below, summarizes the amino acid residue sequences of those peptides.

TABLE 2

| SEQ ID NO: 9 | Met—Ser—Lys—Thr—Glu—Trp—Asp—Ala—Ser—Gln |
| --- | --- |
| MBP 113-122 | Phe—Ser—Trp—Gly—Ala—Glu—Gly—Gln—Arg (EAE PEPTIDE, SEQ ID NO: 17)) |
| SEQ ID NO: 10 | Ser—Arg—Phe—Gly—Trp—Phe—Glu—Asn—Lys—Glu |
| SEQ ID NO: 11 | Leu—Pro—Arg—Leu—Gly—Gly—Lys—Glu—Asp—Arg |
| SEQ ID NO: 12 | Thr—Leu—Gln—Arg—Phe—Ala—Trp—Gly—Ser—Ser—Asn |
| SEQ ID NO: 13 | Phe—Trp—Arg—Phe—Leu—Trp—Gly—Ser—Ser—Gln |
| SEQ ID NO: 14 | Met—Ser—Lys—Thr—Glu—Trp—Asn—Ala—Ser—Gln—Ser—Arg—Phe—Gly—Trp—Phe—Glu—Asn—Lys—Glu |
| SEQ ID NO: 15 | Leu—Pro—Arg—Leu—Gly—Gly—Lys—Glu—Asp—Arg—Ser—Arg—Phe—Gly—Trp—Phe—Glu—Asn—Lys—Glu |
| SEQ ID NO: 16 | Met—Ser—Lys—Thr—Glu—Trp—Asn—Ala—Ser—Gln—Leu—Pro—Arg—Leu—Gly—Gly—Lys—Glu—Asp—Arg |

TABLE 2-continued

| | |
|---|---|
| MBP 68-84 | Tyr—Gly—Ser—Leu—Pro—Gln—Lys—Ala—Gln—Arg—Pro—Gln—Asp—Glu—Asn (SEQ ID NO: 18) |
| MBP 87-99 | Val—His—Phe—Phe—Lys—Asn—Ile—Val—Thr—Pro—Arg—Thr—Pro (SEQ ID NO: 19) |

All agents were tested for their ability to prevent or effectively treat arthritis, as set forth in Example 1. Once again, arthritis was induced and at the first clinical signs of disease, one or more of the peptides were inoculated subcutaneously in IFA. The decapeptides SEQ ID NOs:9, 10 and 11) individually had no effect on the course of the arthritis compared with IFA inoculated controls, but a combination of all three peptides at a total concentration equal to that of the individual peptides was highly effective. (FIG. 2). The individual decapeptides SEQ ID NO:12 (influenza-derived) and SEQ ID NO:13 (adenovirus-derived) were both somewhat effective by themselves, as was EAE peptide (SEQ ID NO:17) derived from MBP.

These data suggest that the EAE peptide-region of MBP may contain much of the anti-arthritic activity. Bovine MBP fragments covering most of the region 68–99 (FIGS. 3 and 4) showed some effect, but it was not striking. Notably, pMBP that had been allowed to solvated and allowed to sit in a refrigerator at 4 degrees centigrade for three months had no activity, strongly suggesting that oxidative and degradative processes destroy MBP activity. Surprisingly, MMR vaccine was partially effective, in contradistinction to the earlier results of the second set of experiments (FIG. 1). Since MMR also protected against onset of arthritis in the first set of experiments, these data suggest that the activity of MMR alters during the course of the disease, acting as a good vaccine against arthritis, a weak depressor of arthritis symptoms during the early stages of the disease, and as an exacerbator in the later stages of the disease. Whether this effect is due to differential persistence of the viral components of MMR, or different antibody response times or interactions cannot be determined by these results.

By far the two most effective agents discovered in this set of experiments were SEQ ID NO:14, a 20 amino acid long peptide made by combining the sequences of SEQ ID NOs:9 and 10) (FIG. 3) and SEQ ID NO:16, a linear combination of the sequences of SEQ ID NOs:9 and 11), both derived from measles viral proteins (FIG. 5). Inoculations of the carrier materials, IFA and saline, had no observable effect on the progress of the arthritis.

To summarize, measles vaccine and pMBP appear to protect against and to effectively treat pre-existing arthritis clinical symptoms. Several peptides consisting of regions of homology between measles, influenza, or adenovirus and MBP are also effective treatments for arthritis. In particular, RBARTH-6 and RBARTH-8 appear to be much more effective than either measles vaccine or pMBP and may represent the regions in which much of the measles and MBP activity lies. Other peptides derived from influenza virus and adenoviruses that have homologies to the same region were also effective.

We also observed that rats injected with a BP-Mb combination developed experimental allergic encephalomyelitis (EAE) an animal model for MS and post-vaccinal neuropathies, but did not develop any symptoms of arthritis over a period of 2 months. It is also known that animals pretreated with mycobacteria do not develop EAE and that treatment with mycobacteria after EAE induction can suppress the disease. These observations have been amply confirmed by 40 years of research on EAE, although previous investigators have overlooked their significance: BP prevents arthritis; Mb and Mt prevent EAE; therefore EAE and arthritis are immunologically related. This relationship can be amplified. EAE is a model for MS; MS patients have T-cell immunity to BP, and measles is thought to play a role in MS induction; BP shares a number of homologous sequences with both measles and influenza viruses; BP, measles, and to some extent influenza antigens protect against induction of arthritis; thus, MS and human arthritis also may be immunologically related.

We do not, at this time, understand the mechanism by which this indirect immunity is conferred. Simple competition for lymphocytes seems unlikely since equal doses of influenza, measles, and DTP vaccines had different effects on the course of the arthritis. Moreover, the dose dependence of the effects suggests that prevention depends upon a specific protein epitope that is absent in DTP, present in low amounts in flu and in high amounts in measles vaccine. This epitope may be the homologous sequences shared by BP, measles, and influenza proteins. How this hypothetical epitope expresses its function is open to speculation. It seems unlikely that the prevention is due to general vaccine-induced immunosuppression, since these vaccines have been engineered specifically to provoke active immunity. Immunological studies have demonstrated that there is no cross-reactivity between mycobacterial antigens and BP, suggesting that the protection EAE affords against arthritis and vice versa is not mediated by a common sequence shared by mycobacteria and BP. Another possibility is a dual-antigen theory of autoimmunity that requires two immunologically complementary antigens to be present simultaneously. If one is present in too great amounts, then, as has been shown in studies of EAE, prevention or suppression occurs. Thus, the viral epitope might be homologous to only one of two or more bacterial antigens and create an imbalance in the immune response to the antigens sufficient to prevent the arthritis. More research is necessary to clarify these points.

Second, the immunological relationship between EAE and arthritis suggests the possibility that MS and human arthritis may be similarly related. If so, then one would expect that patients who have MS do not contract arthritis, and vice-versa. Such an observation might prove to be useful for unravelling the etiologies of these diseases.

Third, the concept of indirect immunity may be useful for understanding some other problems of disease etiology. For example, MS is more prevalent in northern latitudes and in industrialized nations than in southern latitudes and under-developed nations. The usual explanation for this observation is that some viruses are more prevalent in the countries in which MS incidence is high than it is in countries in which MS incidence is low.

Fourth, the observation that DTP exacerbated arthritis suggests the possibility that adverse DTP reactions in human patients may be associated with susceptibility to or presence of particular types of arthritis. Thus, reactions that are currently considered adverse may be turned to some diagnostic use by clinicians either as a test for susceptibility to certain types of arthritis or as a predictor of incipient arthritis.

Fifth, the phenomenon of indirect immunity and vaccination may be general. Induction of EAE in rats is prevented by prior infection with murine coranavirus. A lymphotrophic viral infection protects mice against autoimmune diabetes (though it is unclear whether protection is afforded by T-cell depletion or induction of suppressor cells). Wagner-Juaregg received a Nobel Prize for his demonstration that established general paresis (particularly tertiary syphilis) could be cured with vaccines made from malaria and tuberculosis organisms. The mechanism by which these vaccines worked was never established. Similar cases of unusual protection by one organism against another undoubtedly exist. Thus, these observations suggest that it may be possible to engineer indirect-acting vaccines made from microbes unrelated to the disease-causing organism for diseases (such as autoimmune diseases and various viral and protozoal infections) that are presently difficult to immunize against or treat directly.

EXAMPLE 4

Anti-arthritic Studies

The studies were performed as follows. Groups of three female Lewis rats, ca. 200 grams, were inoculated with 0.3 ml (except IFA) of one of the following agents subcutaneously in the lower back: 0.15 ml Incomplete Freund's adjuvant (IFA) (Sigma); porcine myelin basic protein (PMBP) 25 mg/ml in sterile saline (Lilly); measles vaccine (live virus, attenuated) (Merck); Fluogen (influenzas A and B) (Parke-Davis); Diphtheria-pertussis-tetanus vaccine; chicken ovalbumin (OA) 25 mg/ml in sterile saline (Sigma); SEQ ID NO:14 peptide (9 mg/ml) in sterile saline emulsified with IFA; SEQ ID NO:16 peptide (9 mg/ml) in sterile saline emulsified with IFA. Sixteen days later, all of the animals were challenged with complete Freund's adjuvant (CFA) 10 mg/ml M. tuberculosis in IFA; 0.1 ml inoculated subcutaneously in the base of the tail. The results of the experiments are shown in FIG. 7 and FIG. 8, where each block in each graph represents a single day post-inoculation. Each limb of the animal was scored for presence of arthritis symptoms (swelling, redness) on a scale of 0 (no symptoms) to 4 (extreme swelling to the point of inability to use the limb). Within each block, then, a total of 16 units (4×4 limbs) can be filled. The more black there is within a block, the greater the degree of arthritis.

Clearly IFA, measles, and flu had no effect whatever on the normal course of arthritis development. These results may help to explain the fact that although measles infections are associated with rare spontaneous remissions in juvenile rheumatoid arthritis and can effectively treat adjuvant arthritis in rats, there is no known protective value against arthritis from either having had natural measles infection or measles vaccination.

DPT, PMBP, and SEQ ID NO:14 had minimal protective effects that were of limited clinical value. These findings, like those regarding measles vaccine, suggest that two very different processes are at work with regard to protection against induction of arthritis versus treatment of pre-existing arthritis, since these results are the inverse of what was found in the treatment protocols described previously.

SEQ ID NO:16 and OA had very significant protective effects against induction of adjuvant arthritis. These results make RBARTH8 the only agent so far tested that can be used effectively as both a vaccine and a treatment for adjuvant arthritis. These data suggest that it may have potential as both a vaccine and a treatment for human arthritises as well. The significance of the OA results is as yet unknown, but suggest that OA may share a protective region with RBARTH8 or may provide a novel source of active peptides.

These results show clearly that the anti-arthritic effects of the agents claimed herein are almost definitely not due to general immune suppression. Live measles vaccine is well-documented to cause general immune suppression, yet had insignificant effects on the course of the arthritis in these experiments. (It is also worth noting that measles vaccines actually increase the degree of experimental allergic encephalomyelitis, another autoimmune disease rather than causing suppression of disease, suggesting that autoimmune diseases may not respond to immune suppression in a normal manner). Thus, the therapeutic effects reported in the previous experiments in this disclosure are likely to be directed at specific elements of the arthritis response. This conclusion is further reinforced by the fact that a single dose of either OA or of SEQ ID NO:16 16 days prior to arthritis induction was protective. This effect can only be mediated by a peptide-specific immune response.

In order to further characterize the nature of the mechanisms involved in the drug actions of the agents disclosed here, various immunological studies have been undertaken. The most significant at present is that all commercial antibodies so far obtained against measles virus proteins have been able to precipitate pMBP. The technique used for these demonstrations has been Ouchterlony immunodiffusion. Viral antibodies have been used at the concentration they are provided (usually 1 mg/ml). 0.01 ml of antibody is diffused for three hours alone, and then 25 mg/ml pMBP is added as antigen (the time difference makes up for differences in diffusion rate due to very different molecular weights of antibody and antigen). The results are examined 24 hours later. The cross-reaction is specific to measle antibody, and rarely occurs with other antibodies. These results provide proof that the type of homology or similarity criteria outlined below have true immunological meaning in terms of antibody cross-reactivity for similar antigens.

Again, these immunodiffusion data suggest that the mechanism involved in the anti-arthritis effects of measles, pMBP, and their shared antigenic regions is due to a specific, shared immune response elicited by these agents, rather than by some non-specific effect on the immune system.

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 12 amino acids
      (B) TYPE: amino acid (C) STRANDEDNESS:
          (D) TOPOLOGY: linear (ii) MOLECULE TYPE: peptide (xi) SEQUENCE DESCRIPTION: SEQ ID NO:1:

Ser Leu Ser Arg Phe Ser Trp Gly Ala Glu Gly Gln
     1               5                  10

(2) INFORMATION FOR SEQ ID NO:2:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:2:

Ile Phe Lys Leu Gly Gly Arg Asp Ser Arg
     1               5                  10

(2) INFORMATION FOR SEQ ID NO:3:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:3:

Met Ser Lys Thr Glu Trp Asn Ala Ser Gln
     1               5                  10

(2) INFORMATION FOR SEQ ID NO:4:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:4:

Ser Arg Phe Gly Trp Phe Glu Asn Lys Glu
     1               5                  10

(2) INFORMATION FOR SEQ ID NO:5:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:5:

Leu Pro Arg Leu Gly Gly Lys Glu Asp Arg
     1               5                  10

(2) INFORMATION FOR SEQ ID NO:6:

(i) SEQUENCE CHARACTERISTICS:
          (A) LENGTH: 10 amino acids
          (B) TYPE: amino acid (C) STRANDEDNESS:
            (D) TOPOLOGY: linear (ii) MOLECULE TYPE: peptide (xi) SEQUENCE DESCRIPTION: SEQ ID NO:6:

Thr Leu Gln Arg Phe Ala Trp Gly Ser Ser
    1               5                   10

(2) INFORMATION FOR SEQ ID NO:7:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Leu Gln Arg Phe Ala Trp Gly Ser Ser Asn
    1               5                   10

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Phe Trp Arg Phe Leu Trp Gly Ser Ser Gln
    1               5                   10

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Met Ser Lys Thr Glu Trp Asn Ala Ser Gln
    1               5                   10

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Ser Arg Phe Gly Trp Phe Glu Asn Lys Glu
    1               5                   10

(2) INFORMATION FOR SEQ ID NO:11:

(i) SEQUENCE CHARACTERISTICS:
            (A) LENGTH: 10 amino acids
            (B) TYPE: amino acid (C) STRANDEDNESS:
            (D) TOPOLOGY: linear (ii) MOLECULE TYPE: peptide (xi) SEQUENCE DESCRIPTION: SEQ ID NO:11:

Leu Pro Arg Leu Gly Gly Lys Glu Asp Arg
    1               5                   10

(2) INFORMATION FOR SEQ ID NO:12:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Thr Leu Gln Arg Phe Ala Trp Gly Ser Ser Asn
    1               5                   10

(2) INFORMATION FOR SEQ ID NO:13:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Phe Trp Arg Phe Leu Trp Gly Ser Ser Gln
    1               5                   10

(2) INFORMATION FOR SEQ ID NO:14:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Met Ser Lys Thr Glu Trp Asn Ala Ser Gln Ser Arg Phe Gly Trp Phe
    1               5                   10                  15

Glu Asn Lys Glu
                20

(2) INFORMATION FOR SEQ ID NO:15:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Leu Pro Arg Leu Gly Gly Lys Glu Asp Arg Ser Arg Phe Gly Trp Phe
    1               5                   10                  15

Glu Asn Lys Glu
                20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Met Ser Lys Thr Glu Trp Asn Ala Ser Gln Leu Pro Arg Leu Gly Gly
1               5                   10                  15

Lys Glu Asp Arg
            20
```

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Phe Ser Trp Gly Ala Glu Gly Gln Arg
1               5
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Tyr Gly Ser Leu Pro Gln Lys Ala Gln Arg Pro Gln Asp Glu Asn
1               5                   10                  15
```

(2) INFORMATION FOR SEQ ID NO:19:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Val His Phe Phe Lys Asn Ile Val Thr Pro Arg Thr Pro
1               5                   10
``` what is claimed is:

1. A process of treating inflammatory arthritis in an animal or human subject in need of such treatment comprising administering to the subject an effective anti-arthritic amount of one or more peptide, each comprising an amino acid residue sequence that is identical to or homologous to a contiguous stretch of at least ten amino acid residues of residues 110–121 or 153–162 of myelin basic protein.

2. The process of claim 1 wherein the peptide is a viral protein.

3. The process of claim 2 wherein the viral protein is measles viral protein C, measles viral nucleocapsid protein, influenza A/udorn/72 viral NS protein or adenoviral 2.5 protein 21K.

4. The process of claim 3 wherein the viral protein is contained in an intact virus.

5. The process of claim 1 wherein the peptide is myelin basic protein or a fragment thereof.

6. The process of claim 1 wherein the peptide is an isolated and purified peptide of from 10 to about 50 amino acid residues.

7. The process of claim 1 wherein the peptide is an isolated and purified peptide of from 10 to about 40 amino acid residues.

8. The process of claim 1 wherein the peptide is an isolated and purified peptide of from 10 to about 30 amino acid residues.

9. The process of claim 1 wherein the peptide is an isolated and purified peptide of from 10 to about 20 amino acid residues.

10. The process of claim 1 wherein the animal is a dog or horse.

11. A process of treating inflammatory arthritis in a mammal in need of such treatment comprising administering to the mammal an effective anti-arthrtic amount of one or more of peptides comprising any of the amino acid sequences of SEQ ID NOS: 9–16.

12. The process of claim 11, wherein the mammal is a human.

13. The process of claim 11, wherein the mammal is a horse or dog.

* * * * *